(12) United States Patent
Kidoguchi et al.

(10) Patent No.: US 11,363,245 B2
(45) Date of Patent: Jun. 14, 2022

(54) IMAGE PROCESSING DEVICE, IMAGE PROCESSING METHOD, AND IMAGE PROCESSING PROGRAM

(71) Applicant: EIZO Corporation, Hakusan (JP)

(72) Inventors: Satomi Kidoguchi, Hakusan (JP); Takashi Nakamae, Hakusan (JP); Reo Aoki, Hakusan (JP)

(73) Assignee: EIZO Corporation, Hakusan (JP)

( * ) Notice: Subject to any disclaimer, the term of this patent is extended or adjusted under 35 U.S.C. 154(b) by 311 days.

(21) Appl. No.: 16/758,189

(22) PCT Filed: Nov. 6, 2017

(86) PCT No.: PCT/JP2017/039989
§ 371 (c)(1),
(2) Date: Apr. 22, 2020

(87) PCT Pub. No.: WO2019/087403
PCT Pub. Date: May 9, 2019

(65) Prior Publication Data
US 2020/0296343 A1 Sep. 17, 2020

(51) Int. Cl.
*G06K 9/00* (2022.01)
*H04N 9/77* (2006.01)
(Continued)

(52) U.S. Cl.
CPC .......... *H04N 9/77* (2013.01); *A61B 1/00004* (2013.01); *A61B 1/045* (2013.01); *H04N 5/2351* (2013.01);
(Continued)

(58) Field of Classification Search
CPC ........ H04N 9/77; H04N 5/2351; H04N 5/243; H04N 9/67; H04N 2005/2255;
(Continued)

(56) References Cited

U.S. PATENT DOCUMENTS 5,523,786 A * 6/1996 Parulski ............... H04N 9/0451
348/E5.037
9,412,155 B2 * 8/2016 Steiner ..................... H04N 7/18
(Continued)

FOREIGN PATENT DOCUMENTS

CN 105069131 A 11/2015
EP 0 660 616 A2 6/1995
(Continued)

OTHER PUBLICATIONS

International Search Report dated Jan. 30, 2018 in corresponding International Application No. PCT/JP2017/039989, 4 pages.
(Continued)

*Primary Examiner* — Howard D Brown, Jr.
(74) *Attorney, Agent, or Firm* — Maier & Maier, PLLC

(57) ABSTRACT

To provide an image processing device, an image processing method, and an image processing program capable of performing image processing beneficial for producing an image having high visibility without giving a sense of incongruity to a user such as a doctor. An image processing device is provided, the image processing device being provided with a weighting determination unit and a brightness calculation unit, wherein: when a region made up of a plurality of pixels, which is at least one portion of an input image input to the image processing device, is defined as a noted region, and this input image, either originally or as a result of an operation after being input, is an image expressed in an RGB color space, that is, each pixel is made up of an R component configuring red, a G component configuring green, and a B component configuring blue, and these are collectively defined as RGB components.

9 Claims, 13 Drawing Sheets

(51) Int. Cl.
    *A61B 1/00*     (2006.01)
    *A61B 1/045*     (2006.01)
    *H04N 5/235*     (2006.01)
    *H04N 5/243*     (2006.01)
    *H04N 9/67*     (2006.01)
    *H04N 5/225*     (2006.01)

(52) U.S. Cl.
    CPC ............... *H04N 5/243* (2013.01); *H04N 9/67* (2013.01); *H04N 2005/2255* (2013.01)

(58) Field of Classification Search
    CPC ............... A61B 1/00004; A61B 1/045; A61B 1/000095; A61B 1/04; G06T 11/001; G06T 7/90; G06T 2207/10068
    See application file for complete search history.

(56) References Cited

U.S. PATENT DOCUMENTS

| | | | | |
|---|---|---|---|---|
| 2004/0120576 | A1* | 6/2004 | Kim | H04N 9/641 348/E9.04 |
| 2006/0013478 | A1* | 1/2006 | Ito | H04N 9/68 358/1.9 |
| 2006/0083438 | A1* | 4/2006 | Donomae | G06T 5/003 382/254 |
| 2007/0041636 | A1* | 2/2007 | Yoon | G06T 5/40 382/169 |
| 2007/0153542 | A1 | 7/2007 | Gono et al. | |
| 2010/0253852 | A1* | 10/2010 | Fukuda | H04N 9/646 348/E9.037 |
| 2011/0050918 | A1* | 3/2011 | Tachi | H04N 5/23248 348/208.4 |
| 2011/0292071 | A1* | 12/2011 | Kwon | G09G 3/3233 345/589 |
| 2012/0288199 | A1* | 11/2012 | Kanda | G06T 7/143 382/173 |
| 2013/0071026 | A1* | 3/2013 | Roux | G09G 5/02 382/167 |
| 2014/0184916 | A1* | 7/2014 | Steiner | H04N 7/18 348/607 |
| 2017/0116495 | A1* | 4/2017 | Nomura | G06V 10/955 |

FOREIGN PATENT DOCUMENTS

| | | |
|---|---|---|
| JP | H06-315463 A | 11/1994 |
| JP | 2003-051953 A | 2/2003 |
| JP | 2004-208311 A | 7/2004 |
| JP | 2005-217984 A | 8/2005 |
| JP | 2006-061620 A | 3/2006 |
| JP | 2008-017528 A | 1/2008 |
| JP | 2012-055412 A | 3/2012 |
| JP | 2012-244355 A | 12/2012 |
| JP | 2017-060093 A | 3/2017 |
| KR | 10-2007-0021000 A | 2/2007 |
| KR | 10-2011-0023757 A | 3/2011 |
| KR | 10-2011-0129150 A | 12/2011 |
| WO | 94/18801 A1 | 8/1994 |

OTHER PUBLICATIONS

Extended European Search Report dated Sep. 18, 2020, including the Supplementary European Search Report and the European Search Opinion, in connection with corresponding EP Application No. 17930779.8 (8 pp.).

Korean Notification of Reason for Refusal dated Nov. 15, 2021 in connection with corresponding Korean Application No. 10-2020-7011068 (10 pp.) with English Translation.

* cited by examiner

FIG. 3 First embodiment $W\_r = m \times R\_sub + n$
$W\_g = m \times G\_sub + n$
$W\_b = m \times B\_sub + n$

FIG. 5

| R150 G100 B70 | R200 G60 B40 | R200 G60 B50 | R250 G20 B90 |
|---|---|---|---|
| R180 G100 B70 | R250 G180 B20 | R250 G140 B20 | R180 G100 B70 |
| R180 G100 B40 | R160 G180 B30 | R150 G140 B20 | R120 G100 B80 |
| R70 G100 B70 | R200 G60 B70 | R150 G60 B40 | R150 G20 B20 |

R_avg = 172.5
G_avg = 95.0
B_avg = 50.0

A_avg ≈ 105.8

R_sub = 66.7
G_sub = -10.8
B_sub = -55.8

$$Y = W\_r \times R + W\_g \times G + W\_b \times B$$

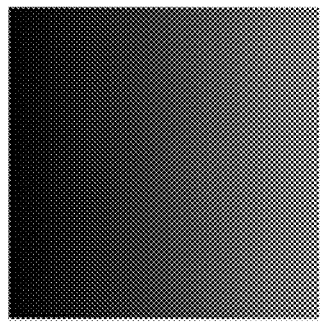
FIG. 7A Input image
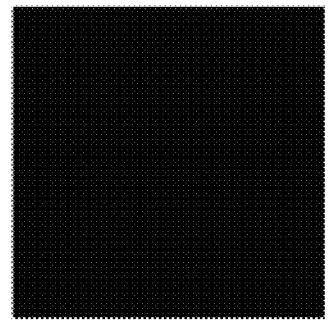
FIG. 7B Output image

FIG. 8 Second embodiment
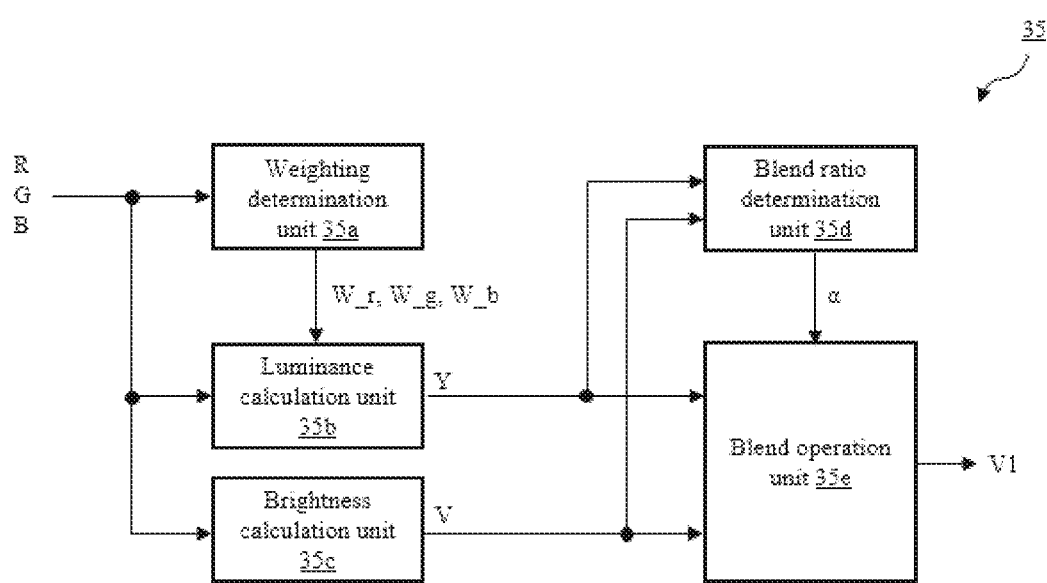

V1=(1-α)V+αY

FIG. 12A Input image (duplicate of FIG. 7A)
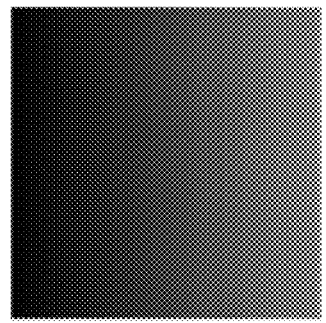
FIG. 12B Output image
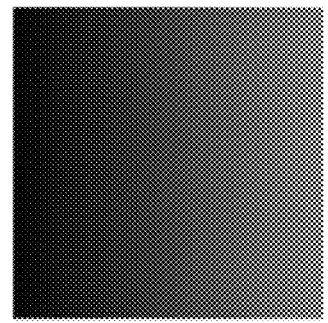

FIG. 13A Input image (includes large R component)
FIG. 13B Intermediate image having the V component extracted
FIG. 13C Output image

IMAGE PROCESSING DEVICE, IMAGE PROCESSING METHOD, AND IMAGE PROCESSING PROGRAM

TECHNICAL FIELD

The present invention relates to an image processing device, an image processing method, and an image processing program.

There are many instances wherein a desired image is displayed on a display device, and this is then used for some kind of inspection or the like. Use in an endoscope is one such example in the medical field. Art for improving blood vessel visibility is being developed to a great extent in the endoscope field. For example, in conventional art for improving blood vessel visibility such as that disclosed in patent literature 1, visibility is improved by converting to a color different from the original color tone (false color) to make it easier to visually recognize blood vessels. Specifically, visibility is improved for a user such as a doctor who visually recognizes an image by displaying after removing or reducing the R component (red component), which tends to be the largest in endoscopic images, and relatively accentuating the G component (green component) and B component (blue component).

PRIOR ART LITERATURE

Patent Literature

[Patent Literature 1] Japanese Unexamined Patent Application Publication No. 2012-055412

SUMMARY OF THE INVENTION

Problem to be Solved by the Invention

However, in conventional art such as that described above, there are also problems such as giving a sense of incongruity to the user such as a doctor because the image is displayed in a different color than the original color tone. It can be said that it is desirable to present images more naturally and at a higher visibility.

In light of the above, an object of the present invention is to provide an image processing device, an image processing method, and an image processing program capable of performing image processing beneficial for producing an image having high visibility without giving a sense of incongruity to a user such as a doctor.

According to this aspect of the present invention, an image processing device is provided, provided with a weighting determination unit and a luminance calculation unit, wherein: when a region made up of a plurality of pixels, which is at least one portion of an input image input to the image processing device, is defined as a noted region, and this input image, either originally or as a result of an operation after being input, is an image expressed in an RGB color space, that is, each pixel is made up of an R component configuring red, a G component configuring green, and a B component configuring blue, and these are defined together as an RGB component, the weighting determination unit respectively determines a weighting coefficient corresponding to each RGB component based on a quantity of each RGB component in the noted region, the luminance calculation unit calculates luminance of each pixel included in the noted region based on each of the weighting coefficients, and when a ratio of each RGB component in the noted region is set as a, b, and c in no particular order (however, fulfilling $a \geq b \geq c$), and each weighting coefficient corresponding to these is set as $W\_a$, $W\_b$, and $W\_c$, $W\_a \leq W\_b \leq W\_c$ is true.

In the image processing device according to this aspect, the weighting determination unit respectively determines a weighting coefficient corresponding to each RGB component based on a quantity of each RGB component in a noted region in an input image, and the luminance calculation unit calculates luminance of each pixel included in the noted region based on each of the weighting coefficients. By using luminance calculated in this manner, effects are achieved wherein it is possible to produce an image having high visibility without giving a sense of incongruity to a user such as a doctor.

Various embodiments of the present invention will be exemplified below. The embodiments shown below can be combined together.

Preferably, the input image is a video having a plurality of frames in a time sequence, the weighting determination unit determines the weighting coefficients using the noted region in a current or past frame of the input image, and the luminance calculation unit calculates luminance of each of the pixels in a current frame.

Preferably, a first conversion unit and a second conversion unit are further provided, wherein: the first conversion unit converts an input image expressed in an RGB color space to an image expressed in a separate color space including brightness or luminance as a parameter, and the second conversion unit inversely converts the image expressed in the separate color space to an output image expressed in the RGB color space, based on corrected brightness or corrected luminance as the luminance calculated by the luminance calculation unit, and based on a parameter other than brightness or luminance in the image converted by the first conversion unit.

Preferably, a first conversion unit, a blend operation unit, and a second conversion unit are further provided, wherein: the first conversion unit converts an input image expressed in an RGB color space to an image expressed in a separate color space including brightness or luminance as a parameter, the blend operation unit calculates a correction brightness or correction luminance, which is a corrected brightness or corrected luminance by blending brightness or luminance in the image converted by the first conversion unit and the luminance calculated by the luminance calculation unit at a prescribed blend ratio, and the second conversion unit inversely converts to an output image expressed in an RGB color space based on the correction brightness or correction luminance and a parameter other than brightness or luminance in the image converted by the first conversion unit.

Preferably, the blend ratio is determined based on the ratio of the brightness or the luminance in the noted region in the image converted by the first conversion unit and the luminance calculated by the luminance calculation unit.

Preferably, the weighting determination unit respectively determines the weighting coefficients based on each difference between an overall average value of RGB components in the noted region and an average value of each RGB component.

Preferably, the weighting determination unit respectively determines the weighting coefficients based on a photograph of each difference, and a function relating to the photograph includes an nth order function ($n \geq 1$), a logarithmic function, and an exponential function.

According to another aspect of the present invention, an image processing method is provided, provided with a weighting determination step and a luminance calculation step, wherein: when a region made up of a plurality of pixels, which is at least one portion of an input image handled in the image processing method, is defined as a noted region, and this input image, either originally or as a result of an operation after being input, is an image expressed in an RGB color space, that is, each pixel is made up of an R component configuring red, a G component configuring green, and a B component configuring blue, and these are defined together as an RGB component; in the weighting determination step, a weighting coefficient corresponding to each RGB component is respectively determined based on a quantity of each RGB component in the noted region; in the luminance calculation step, luminance of each pixel included in the noted region is calculated based on each of the weighting coefficients and when a ratio of each RGB component in the noted region is set as a, b, and c in no particular order (however, fulfilling a≥b≥c), and each weighting coefficient corresponding to these is set as $W\_a$, $W\_b$, and $W\_c$, $W\_a \leq W\_b \leq W\_c$ is true.

In the image processing method according to this aspect, in the weighting determination step, a weighting coefficient corresponding to each RGB component is respectively determined based on a quantity of each RGB component in the noted region in an input image, and in the luminance calculation step, luminance of each pixel included in the noted region is calculated based on each of the weighting coefficients. By using luminance calculated in this manner, effects are achieved wherein it is possible to produce an image having high visibility without giving a sense of incongruity to a user such as a doctor.

According to another aspect of the present invention, an image processing program for realizing a prescribed function in a computer is provided, wherein: the prescribed function includes a weighting determination function and a luminance calculation function; when a region made up of a plurality of pixels, which is at least one portion of an input image input to the computer, is defined as a noted region, and this input image, either originally or as a result of an operation after being input, is an image expressed in an RGB color space, that is, each pixel is made up of an R component configuring red, a G component configuring green, and a B component configuring blue, and these are defined together as an RGB component; according to the weighting determination function, a weighting coefficient corresponding to each RGB component is respectively determined based on a quantity of each RGB component in the noted region; according to the luminance calculation function, luminance of each pixel included in the noted region is calculated based on each of the weighting coefficients and when a ratio of each RGB component in the noted region is set as a, b, and c in no particular order (however, fulfilling a≥b≥c), and each weighting coefficient corresponding to these is set as $W\_a$, $W\_b$, and $W\_c$, $W\_a \leq W\_b \leq W\_c$ is true.

In the image processing program according to this aspect, according to the weighting determination function, a weighting coefficient corresponding to each RGB component is respectively determined based on a quantity of each RGB component in a noted region in an input image; according to the luminance calculation function, luminance of each pixel included in the noted region is calculated based on each of the weighting coefficients. By using luminance calculated in this manner, effects are achieved wherein it is possible to produce an image having high visibility without giving a sense of incongruity to a user such as a doctor.

BRIEF DESCRIPTION OF THE DRAWINGS

FIG. 4 is a block diagram showing a process flow of a weighting determination unit 35a.

FIG. 5 is a schematic diagram illustrating an example of an RGB component in an input image I.

FIG. 7 is a diagram illustrating a problem confirmed in the adaptive processing unit 35 according to the first embodiment. Specifically, FIG. 7A illustrates the input image I and FIG. 7B illustrates an output image O.

FIG. 8 is a block diagram showing a process flow of the adaptive processing unit 35 according to the second embodiment of the present invention.

FIG. 11 is a block diagram showing a process flow of a blend operation unit 35e.

FIG. 12 is a comparison image of FIG. 7A and FIG. 7B. Specifically, FIG. 12A illustrates the input image I and FIG. 12B illustrates the output image O.

FIG. 13 illustrates a case wherein image processing is performed using the image processing device 3 according to the second embodiment in a scenery image including a large R component. Specifically, FIG. 13A illustrates the input image I, FIG. 13B illustrates an intermediate image having the V component extracted, and FIG. 13C illustrates an output image O.

MODES FOR CARRYING OUT THE INVENTION

Embodiments of the present invention will be described in detail below with reference to drawings. Particularly, "unit" in the present specification, for example, can refer to a combination of a hardware resource executed by a circuit in the broad sense and information processing of software that can specifically be realized by this hardware resource.

Moreover, circuit in the broad sense is a circuit realized by appropriately combining at least a circuit, circuitry, a processor, a memory, and the like. That is to say, please note that this includes application specific integrated circuits (ASICs), programmable logic devices (for example, simple programmable logic devices (SPLDs), complex programmable logic devices (CLPDs), and field programmable gate arrays (FPGAs)), and the like.

Furthermore, in the present specification, a region made up of a plurality of pixels, which is at least one portion of an input image input to an image processing device and the like, is defined as a noted region, and this input image is an image expressed in an RGB color space, that is, each pixel is made up of an R component configuring red, a G component configuring green, and a B component configuring blue, and these are defined together as an RGB component. Additionally, an image includes both still images and videos. In the case of videos, an image refers to one frame thereof unless particularly noted otherwise.

Moreover, various information and concepts including such are handled in the embodiments described in detail below are expressed by a low or high value of a signal value as a binary bit assembly configured of 0 or 1, and communication and operations can be performed on the circuit in the broad sense. Specifically, "noted region," "weighting coefficient," "luminance Y," "RGB component," "hue H," "saturation S," "brightness V," "blend ratio," and the like can be included in such information/concepts. These will be described again in detail as necessary.

1. System 1 (Overall Configuration)

Figure 1:
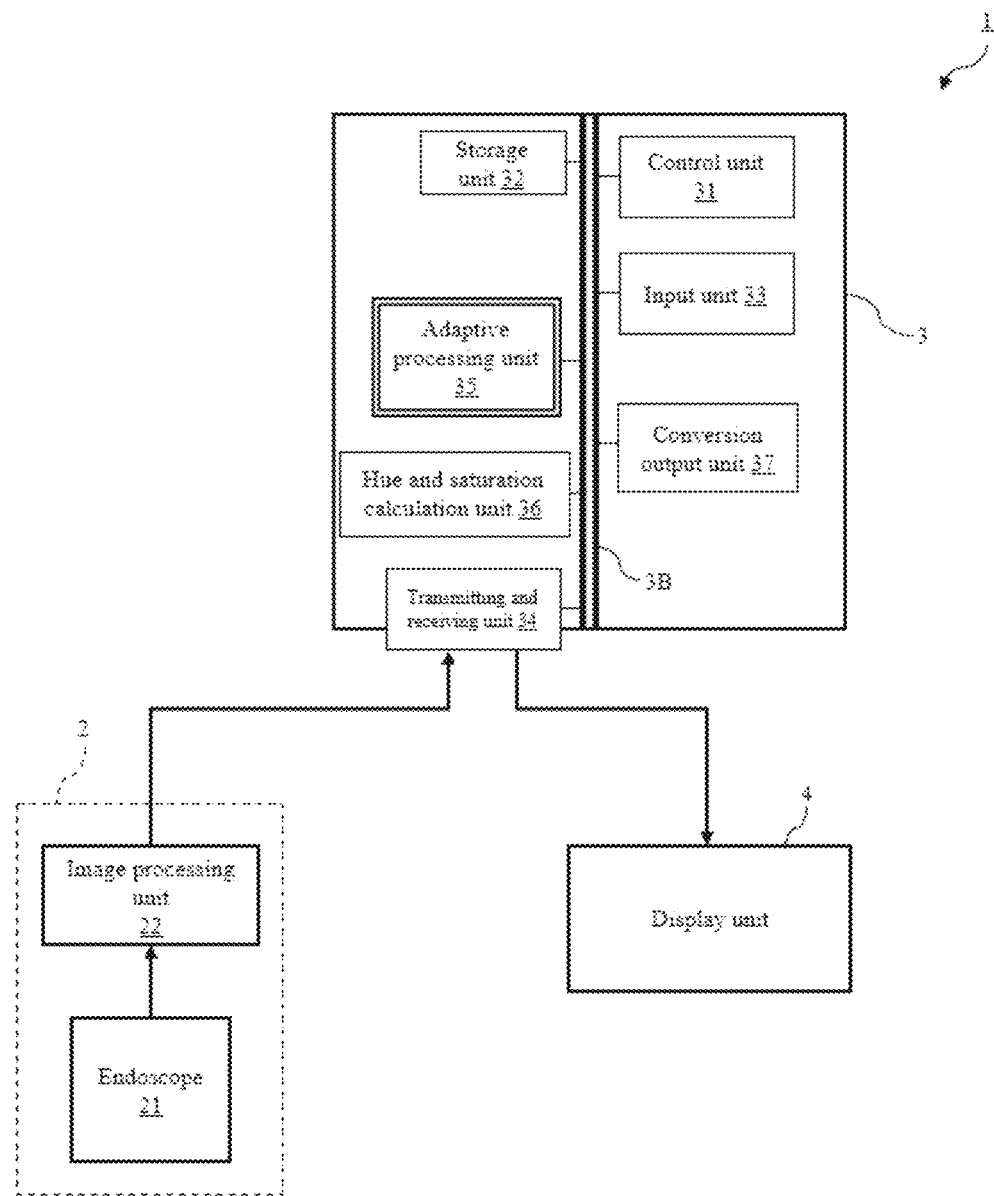

FIG. 1 is a diagram illustrating a configuration outline of a system 1 using an image processing device 3 according to embodiments (both the first and second embodiments) of the present invention. The system 1 is provided with an endoscope system 2, an image processing device 3, and a display unit 4.

1.1 Endoscope System 2

The endoscope system 2 is provided with an endoscope 21 and an image processing unit 22. The endoscope 21 has a vision sensor (camera) not illustrated in the drawings, and for example, it is configured so that the abdomen or the like of a test subject can be imaged by inserting this from the oral cavity of the test subject toward the abdomen. Note that in terms of information processing, the imaged image data is an assembly of two-dimensional pixels (pixel array). Furthermore, the image processing unit 22 performs prescribed image processing on the image data imaged by the endoscope 21. For example, 3D noise reduction processing, particularly using two frames from among the image data imaged by the endoscope 21, which are adjacent in a time sequence, to reduce noise superimposed on the image, or the like can be included.

1.2 Image Processing Device 3

The image processing device 3 is a device for performing prescribed image processing on image data sent from the endoscope system 2. The image processing device 3 is provided with a control unit 31, a storage unit 32, an input unit 33, a transmitting and receiving unit 34, an adaptive processing unit 35, a hue and saturation calculation unit 36, and a conversion output unit 37, and these are connected via a communication bus 3B. The components 31 to 37 will be respectively described in detail below.

<Control Unit 31>

The control unit 31 carries out processing and control of all actions relating to the image processing device 3. The control unit 31 is, for example, a central processing unit (CPU) not illustrated in the drawings. The control unit 31 realizes various functions relating to the image processing device 3 or system 1 by reading a prescribed program stored in the storage unit 32. For example, this includes reading a prescribed program and displaying an image of a graphical user interface (GUI) including a real time display image of the endoscope 21 on the display unit 4.

Note that a single control unit 31 is shown in FIG. 1, but it is not actually limited to this. It may be implemented to have a plurality of the control unit 31 for each function. Moreover, it may also be a combination of these.

<Storage Unit 32>

The storage unit 32 stores various programs and the like for being realized by the control unit 31 as described above. This can be implemented as, for example, a storage device such as a hard disk drive (HDD) or a solid-state drive (SSD). Moreover, the storage unit 32 can be implemented as a memory such as a random-access memory (RAM) for temporarily storing necessary information (arguments, arrays, and the like) relating to program operations. Moreover, it may also be a combination of these.

<Input Unit 33>

The input unit 33, for example, may be included in the image processing device 3 itself, or may be externally attached. For example, the input unit 33 can be implemented as a touch panel. Alternatively, a user interface such as a switch button, a mouse, or a keyboard may be adopted. Commands from an operator (for example, a doctor) are received via the input unit 33. These commands are transmitted to the control unit 31 via the communication bus 3B, and the control unit 31 can perform prescribed control or operations as necessary. As one example of these commands, the operator can temporarily stop an image displayed on the display unit 4 which is also being imaged by the endoscope 21 via the input unit 33. In other words, in the endoscope system 2, the endoscope 21 can temporarily stop (interrupt) the imaging of an image. Meanwhile, the image processing unit 22 can perform 3D noise reduction. As a result, when temporarily stopped, an image that has not undergone 3D noise reduction is transmitted to the transmitting and receiving unit 34 of the system 1.

<Transmitting and Receiving Unit 34>

The transmitting and receiving unit 34 is a unit for communication with the image processing device 3 and external devices other than the image processing device 3. That is, after receiving image data to be an input image from the endoscope system 2 via the transmitting and receiving unit 34 and image processing it (described in detail later), it may be transmitted to the display unit 4 as an output image. Note, communication by the transmitting and receiving unit 34 is not limited to image data. For example, it is preferable to be an aggregate of a plurality of communication means including wired LAN network communication, Bluetooth communication, wireless LAN network communication, and the like, the aggregate being implemented to include a suitable communication standard for the target of communication.

<Adaptive Processing Unit 35>

Figure 2:
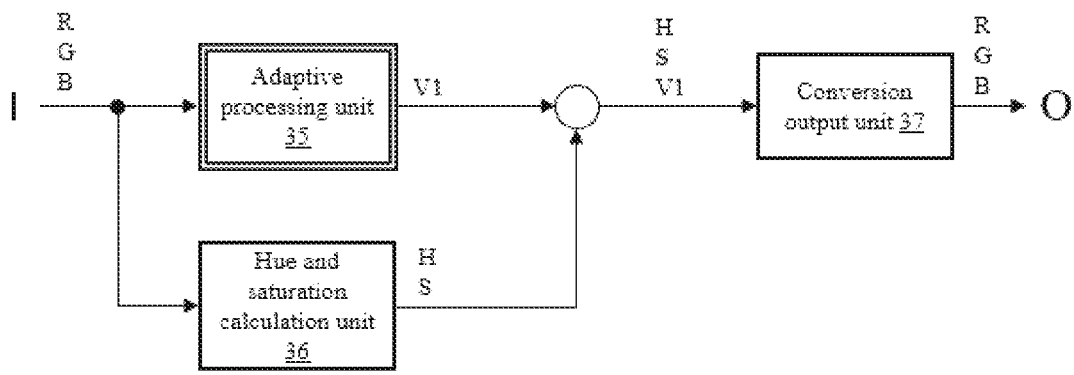
FIG. 2 is a block diagram showing a process flow of an adaptive processing unit 35, a hue and saturation calculation unit 36, and a conversion output unit 37 according to both the first and second embodiments of the present invention.

FIG. 2 is a block diagram showing a process flow of the adaptive processing unit 35, the hue and saturation calculation unit 36, and the conversion output unit 37 according to both the first and second embodiments of the present invention. The adaptive processing unit 35 executes prescribed adaptive processing on the input image (that expressed in an RGB space: includes that expressed in an RGB space directly before being converted from a separate color space and processed) received from the endoscope system 2 via the transmitting and receiving unit 34 and calculates a correction brightness VI, which is a corrected brightness V (value). Further details according to the configuration of the adaptive processing unit 35 and the correction brightness VI will be described again in section 2.

<Hue and Saturation Calculation Unit 36>

The hue and saturation calculation unit 36 (one example of the "first conversion unit" in the Claims) calculates a hue H and a saturation S of the input image from an input image (expressed in an RGB space) received from the endoscope system 2 via the transmitting and receiving unit 34. Note, a color space having the hue H, saturation S, and brightness V as parameters is generally called an HSV color space (one example of the "separate color space" in the Claims).

<Conversion Output Unit 37>

As illustrated in FIG. 2, the conversion output unit 37 (one example of the "second conversion unit" in the Claims) inversely converts to a desired output image expressed in an RGB color space by calculating each RGB component from an intermediate image (expressed in an HSV color space) composed of the correction brightness VI calculated in the adaptive processing unit 35 and the hue H and saturation S calculated in the hue and saturation calculation unit 36. Note, said output image is transmitted to the display unit 4 via the communication bus 3B and the transmitting and receiving unit 34, and the display unit 4 displays the output image.

1.3 Display Unit 4

The display unit 4 may be a medium for displaying image processed image data as a picture based on data of each pixel (information such as luminance possessed by each pixel) when it is input by the image processing device 3, for example, an LCD monitor, a CRT monitor, an organic EL monitor, or the like. Note, the image processing device 3 may include the display unit 4.

2. Adaptive Processing Unit 35

The adaptive processing unit 35 may include first and second embodiments as below. The adaptive processing unit 35 according to each embodiment is described in detail below.

2.1 First Embodiment

Figure 3:
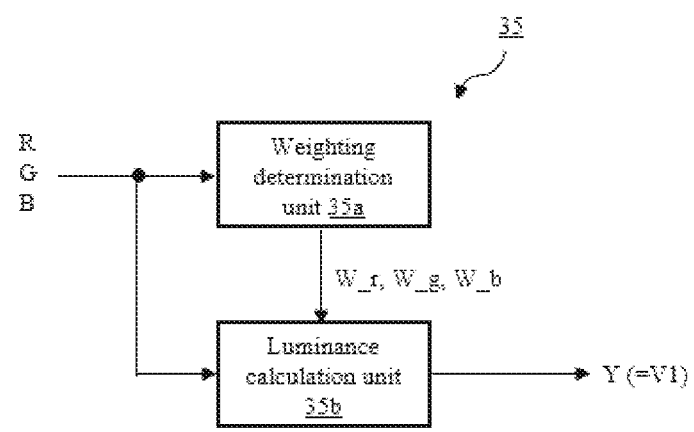
FIG. 3 is a block diagram showing a process flow of the adaptive processing unit 35 according to the first embodiment of the present invention.

FIG. 3 is a block diagram showing a process flow of the adaptive processing unit 35 according to the first embodiment of the present invention. As illustrated in FIG. 3, the adaptive processing unit 35 is provided with a weighting determination unit 35a and a luminance calculation unit 35b.

<Weighting Determination Unit 35a>

Figure 4:
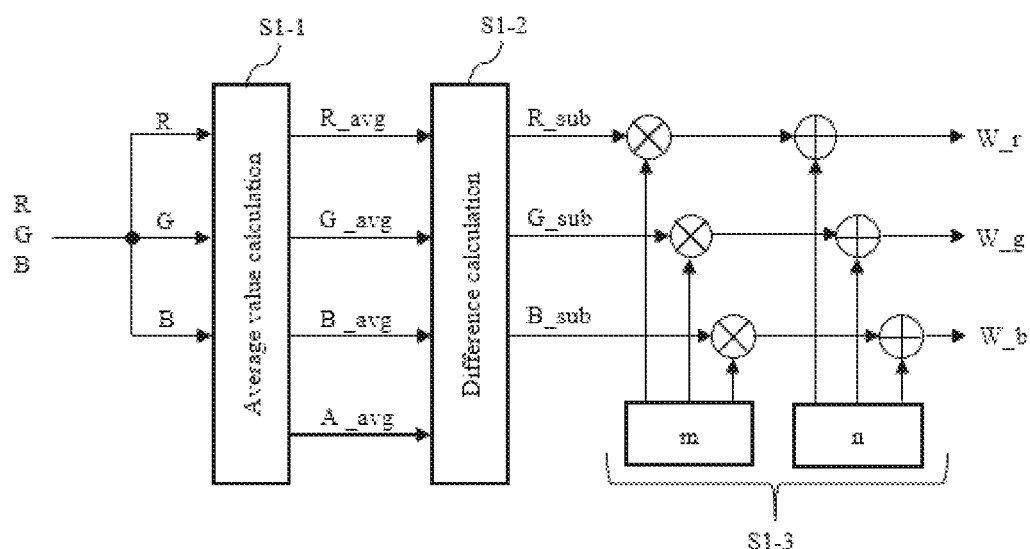

FIG. 4 is a block diagram showing a process flow of the weighting determination unit 35a. Furthermore, FIG. 5 is a schematic diagram illustrating an example of RGB components of an input image I. The weighting determination unit 35a is used in calculating a luminance Y and respectively determines the weighting coefficient corresponding to each RGB component. Specifically, processing such as follows is executed.

[Start]

(Step S1-1)

Each RGB component of all pixels in the noted region of the input image I (here, all pixels of the input image I: for one frame when a video) and the average value of all components are calculated, respectively. For example, assuming that each RGB component takes an 8-bit (0 to 255) integer value, in the 4×4 pixel input image I illustrated in FIG. 5, it is calculated that an average value R_avg of the R component=172.5, an average value G_avg of the G component=95.0, an average value B_avg of the B component=50.0, and an average value A_avg of all components≈105.8. Of course, it need not be said that the input image I actually handled is an image having much higher resolution than this. Proceed to step S1-2, the next step.

(Step S1-2)

Subsequently, each RGB component R_avg, G_avg, and B_avg and differences R_sub, G_sub, and B_sub from the overall average value A_avg are calculated. That is, in the example illustration in FIG. 5, R_sub=66.7, G_sub=−10.8, and B_sub=−55.8. Proceed to step S1-3, the next step.

(Step S1-3)

Subsequently, weighting coefficients W_r, W_g, and W_b corresponding to each RGB component may be determined by performing a linear mapping transformation (substitution into a linear function) on the differences R_sub, G_sub, and B_sub calculated in step S1-2 (Formulae (1) to (3)).

$$W\_r = m \times R\_sub + n \quad (1)$$

$$W\_g = m \times G\_sub + n \quad (2)$$

$$W\_b = m \times B\_sub + n \quad (3)$$

[End]

In particular, here, please note that the weighting determination unit 35a is characterized by respectively determining the weighting coefficient corresponding to each RGB component based on the quantity of each RGB component in the noted region (here, all pixels of the input image I: for one frame when a video).

Note, a slope m of the linear mapping transformation in step S1-3 is set to take a negative value. That is, please note that the magnitude correlation of each RGB component R_avg, G_avg, and B_avg and the magnitude correlation of each weighting coefficient W_r, W_g, and W_b corresponding thereto correspond in inverse order. When in the example illustrated in FIG. 5, R_avg>G_avg>B_avg (one example of a, b, and c in the Claims), and thus it satisfies W_r<W_g<W_b (one example of W_a, W_b, and W_c in the Claims). Note, it is preferable that m and n (segment) are appropriately determined based on pre-implemented test/research results or the like.

<Luminance Calculation Unit 35b>

Figure 6:
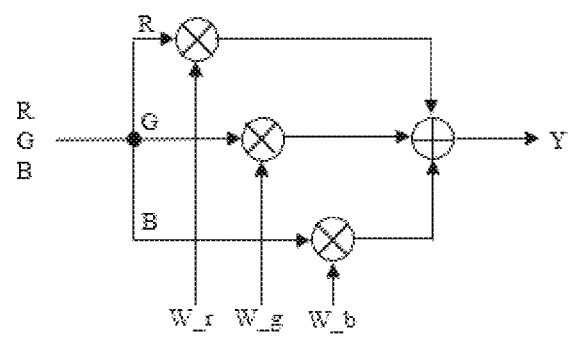
FIG. 6 is a block diagram showing a process flow of a luminance calculation unit 35b.

FIG. 6 is a block diagram showing the process flow of the luminance calculation unit 35b. As illustrated in FIG. 6, the luminance calculation unit 35b calculates the luminance Y of each pixel of the input image I using the weighting coefficients W_r, W_g, and W_b determined by the weighting determination unit 35a. Here, the luminance Y is defined as in Formula (4).

$$Y = W\_r \times R, W\_g \times G, \text{ and } W\_b \times B \quad (4)$$

Here, R, G, and B are respective values (for example, integer values of 0 to 255) of RGB components in each pixel.

Note, in the first embodiment, the luminance Y of each pixel is treated as the correction brightness VI. That is, in a conversion output unit 37, a desired output image O expressed in an RGB color space is generated by calculating each RGB component from an intermediate image (expressed in an HSV color space) composed of the luminance Y (correction brightness VI) and the hue H and saturation S calculated in the hue and saturation unit 36.

Such an output image O maintains information of the original input image I for the hue H and the saturation S. That is, according to the system 1, including the image processing device 3 according to the first embodiment, the original color tone is maintained, an image having greater visibility is generated, and effects are achieved wherein it is possible to display this on the display unit 4.

FIG. 7A and FIG. 7B are diagrams illustrating a problem observed in the adaptive processing unit 35 according to the first embodiment, and in particular, FIG. 7A illustrates the input image I, and FIG. 7B illustrates an output image O. In the first embodiment, the quantity of each RGB component affects the calculation of the luminance Y, but depending on the image, defects such as crushed shadows are also observed. For example, as in FIG. 7A, when assuming a gradated image (example wherein the color component gradually increases from the left side to the right side) composed of one color (here, assumed to be the R component) to be the input image I, for the output image O outputted in the image processing device 3 including the adaptive processing unit 35 according to the first embodiment, W_r becomes extremely small, and because it is a monochromatic image (G component and B component are both 0), crushed shadows occur, as illustrated in FIG. 7B. To solve such problems, a second embodiment described in section 2.2 is preferable.

2.2 Second Embodiment

FIG. 8 is a block diagram showing the process flow of the adaptive processing unit 35 according to the second embodiment of the present invention. As illustrated in FIG. 8, the adaptive processing unit 35 is provided with the weighting determination unit 35a, the luminance calculation unit 35b, a brightness calculation unit 35c, a blend ratio determination unit 35d, and a blend operation unit 35e. Note, the configuration and action of the weighting determination unit 35a and the luminance calculation unit 35b are substantially the same as the first embodiment, and thus, please refer again to the description in section 2.1 as necessary.

<Brightness Calculation Unit 35c>

The brightness calculation unit 35c (one example of the "first conversion unit" in the Claims) calculates the brightness V of each pixel of the input image I. Here, the brightness V is defined as in Formula (5).

$$V = \text{Max}[R, G, B] \quad (5)$$

Here, R, G, and B are respective values (for example, integer values of 0 to 255) of RGB components in each pixel.

<Blend Ratio Determination Unit 35d>

Figure 9:
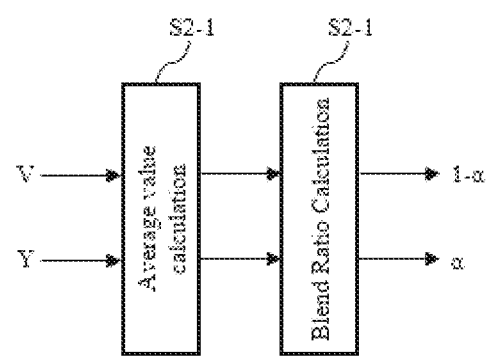
FIG. 9 is a block diagram showing a process flow of a blend ratio determination unit 35d.

FIG. 9 is a block diagram showing the process flow of the blend ratio determination unit 35d. The blend ratio determination unit 35d determines a blend ratio usable in blending (see the action of the blend operation unit 35e for details) the luminance Y calculated with the luminance calculation unit 35b and the brightness V calculated with the brightness calculation unit 35c. Specifically, processing such as follows is executed.

[Start]

(Step S2-1)

Average values (Y_avg and V_avg) of the luminance Y and the brightness V of all pixels in the noted region of the input image I (here, all pixels of the input image I: for one frame when a video) are calculated, respectively. Proceed to step S2-2, the next step.

(Step S2-2)

Figure 10:
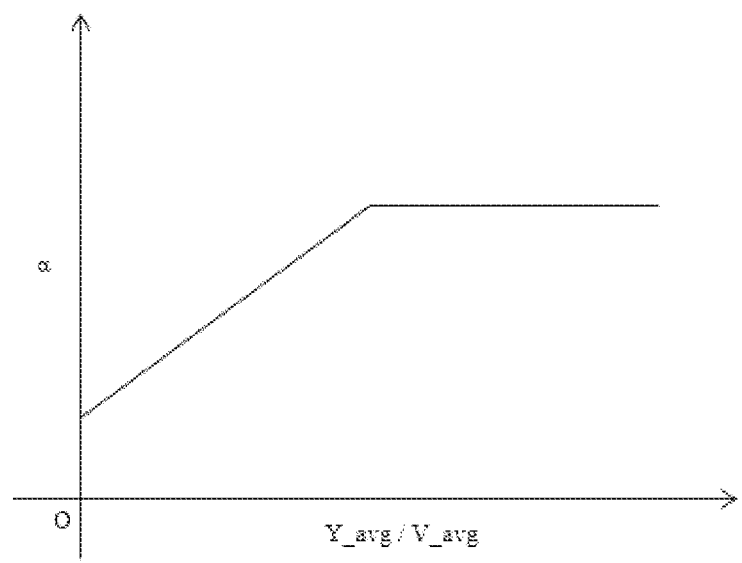
FIG. 10 is a graph illustrating an example of a rule used for determining a blend ratio α.

Subsequently, a blend ratio (here, a blend ratio α of Y) is determined based on the proportion (here, Y_avg/V_avg) of the Y_avg and V_avg calculated in step S2-1. For example, the blend ratio α may be determined based on a determination principle of the blend ratio illustrated in FIG. 10. In particular, please note that the blend ratio α is determined based on the proportion of the brightness V and the luminance Y in the noted region. Note, that illustrated in FIG. 10 is just an example, and it is preferable that this principle is appropriately determined based on pre-implemented test/research results or the like.

[End]

<Blend Operation Unit 35e>

Figure 11:
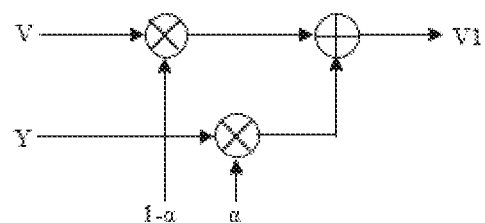
FIG. 11 is a diagram illustrating a configuration outline of a system 1 using an image processing device 3 according to both the first and second embodiments of the present invention.

FIG. 11 is a block diagram showing a process flow of a blend operation unit 35e. The brightness V and the luminance Y of each pixel in the noted region are blended using the blend ratio α determined by the blend ratio determination unit 35d, and this is made the correction brightness VI (see Formula (6)).

$$V' = (1-\alpha)V + \alpha Y \quad (6)$$

Thereafter, in the conversion output unit 37, the desired output image O expressed in an RGB color space is generated by calculating each RGB component from an intermediate image (expressed in an HSV color space) composed of the correction brightness VI and the hue H and saturation S calculated in the hue and saturation unit 36.

Such an output image O maintains information of the original input image I for the hue H and the saturation S. That is, according to the system 1, including the image processing device 3 according to the second embodiment, the original color tone is maintained, an image having greater visibility is generated, and effects are achieved wherein it is possible to display this on the display unit 4.

FIG. 12A and FIG. 12B are comparative images with FIG. 7A and FIG. 7B, and in particular, FIG. 12A illustrates the input image I, and FIG. 12B illustrates the output image O. As described above, defects such as crushed shadows are also observed depending on the image in the first embodiment. Meanwhile, in the second embodiment, as illustrated in FIG. 12A (duplicate of FIG. 7A), even when assuming a gradated image (example wherein the color component gradually increases from the left side to the right side) composed of one color (here, assumed to be the R component) to be the input image I, as illustrated in FIG. 12B, the result for the output image O outputted in the image processing device 3 including the adaptive processing unit 35 according to the second embodiment, is that gradation is maintained.

Additionally, FIG. 13A to FIG. 13C illustrate a case wherein image processing is executed using the image processing device 3 according to the second embodiment in a scenery image including a large R component, and in particular, FIG. 13A illustrates the input image I, FIG. 13B illustrates an intermediate image having the V component extracted, and FIG. 13C illustrates the output image O. Even in such an actual image, similarly to the results of FIG. 12A and FIG. 12B, it is observed that an output image O maintaining natural gradation and having high visibility is obtained (see FIG. 13C). Compared to FIG. 13B (intermediate image having the V component extracted) and FIG. 13 C (output image O) gradation is not maintained in the intermediate image, and the difference to the output image O is obvious.

3. Variations

The present embodiments can also be implemented by the following modes.

First, in the present embodiments, the range (noted region) according to luminance calculation or the like is described as all pixels of the input image I (one frame when a video), but the pixels used may be selected partially. For example, the noted region may be a partial rectangular region, and it may be implemented by generating a compressed image by appropriately selecting representative pixels (for example, the median value in a specific position such as top left or in a small region) for each small rectangular region of a prescribed size and setting this as the noted region.

Second, in the various processes described above, a two-dimensional array is presumed, but so long as it is ultimately possible to display the desired image on the display unit 4, it may be stored as a one-dimensional array during operations. Furthermore, instead of performing operations using a one-dimensional array or a two-dimensional array, operations may be performed sequentially.

Third, the present embodiments include conversion from an RGB color space to an HSV color space including a brightness V, but they are not limited thereto. In the same manner that the luminance Y in the first embodiment can be viewed as the correction brightness VI, it may be converted to a color space including luminance as a parameter other than brightness. For example, a YUV color space, YCICb, YPrPb, or HSL color space or the like may be adopted. The effect shown in the present embodiments may be similarly expected by inserting the correction brightness VI into the luminance Y or L in these color spaces to inversely convert.

Fourth, the system 1 according to the present embodiments adopts the endoscope system 2, but it is not limited thereto, and it is considered that any signal source that transmits an input image, which may contain many specific components among specific RGB components can be effectively applied. That is, even when applying to that other than the endoscope system 2, effects are achieved wherein it is possible to output an image with high visibility.

Fifth, in the present embodiments, (assuming that the input image I is a video) it is described that the weighting determination unit 35*a* determines the weighting coefficients using the (current) frame at a particular time in the input image I, and the luminance calculation unit 35*b* also calculates the luminance of each pixel in the same frame, but they are not limited hereto. For example, it may be implemented such that the weighting determination unit 35*a* determines the weighting coefficients using a (past) frame at a particular time in the input image I, and the luminance calculation unit 35*b* calculates the luminance of each pixel in the (current) frame after that time. It is not particularly limited how far in the past the past frame is, and, for example, one frame prior, two frames prior, three frames prior, and the like are conceivable.

Sixth, in the present embodiments, the weighting determination unit 35*a* determines the weighting coefficients W_r, W_g, and W_b corresponding to each RGB component by performing a linear mapping transformation (substitution into a linear function), but this is just an example, and they are not limited thereto. The function according to the mapping may, for example, be an nth order function (n≥2) and may be a logarithmic function, or an exponential function.

Seventh, it is possible to provide an image processing program for realizing a prescribed function in a computer, wherein: the prescribed function comprises a weighting determination function and a luminance calculation function, and when a region made up of a plurality of pixels, which is at least one portion of an input image input to the computer, is defined as a noted region, and this input image, either originally or as a result of an operation after being input, is an image expressed in an RGB color space, that is, each pixel is made up of an R component configuring red, a G component configuring green, and a B component configuring blue, and these are defined together as an RGB component, according to the weighting determination function, a weighting coefficient corresponding to each RGB component is respectively determined based on a quantity of each RGB component in the noted region, and according to the luminance calculation function, luminance of each pixel included in the noted region is calculated based on each of the weighting coefficients. Furthermore, it is also possible to provide it as a computer-readable non-transitory recording medium implementing the functions of the program. Moreover, it is possible to send the program via the internet or the like. Additionally, each part configuring the system 1 may be included in the same housing or may be distributed between a plurality of housings.

4. Conclusion

As above, according to the present embodiments, it is possible to provide an image processing device, an image processing method, and an image processing program capable of performing image processing beneficial for producing an image having high visibility without giving a sense of incongruity to a user such as a doctor.

Various embodiments according to the present invention were described, but these are presented as examples and are not intended to limit the scope of the present invention. The new embodiment can be implemented in various other modes, and various omissions, replacements, and changes can be made in a scope not deviating from the summary of the invention. Along with the embodiment or a variation thereof being included in the scope or summary of the invention, it is included in the inventions described in the Claims and scopes equal thereto.

DESCRIPTION OF REFERENCE NUMERALS

1: System
2: Endoscope system
21: Endoscope
22: Image processing unit
3: Image processing device
3B: Communication bus
31: Control unit
32: Storage unit
33: Input unit
34: Transmitting and receiving unit
35: Adaptive processing unit
35*a*: Weighting determination unit
35*b*: Luminance calculation unit
35*c*: Brightness calculation unit
35*d*: Blend ratio determination unit
35*e*: Blend operation unit
36: Hue and saturation calculation unit
37: Conversion output unit
4: Display unit
A_avg: Average value
R_avg: Average value
B_avg: Average value
G_avg: Average value
R_sub: Difference
G_sub: Difference
B_sub: Difference
H: Hue
S: Saturation
V: Brightness
VI: Correction brightness
Y: Luminance
W_r: Weighting coefficient
W_g: Weighting coefficient
W_b: Weighting coefficient
I: Input image O: Output image
m: Slope
n: Segment
α: Blend ratio

The invention claimed is:

1. An image processing device, comprising:
a weighting determination unit and a luminance calculation unit, wherein
when a region made up of a plurality of pixels, which is at least one portion of an input image input to the image processing device, is defined as a noted region, and this input image, either originally or as a result of an operation after being input, is an image expressed in an RGB color space, that is, each pixel is made up of an R component configuring red, a G component configuring green, and a B component configuring blue, and these are defined together as an RGB component,
the weighting determination unit respectively determines a weighting coefficient corresponding to each RGB component based on a quantity of each RGB component in the noted region,
the luminance calculation unit calculates luminance of each pixel included in the noted region based on each of the weighting coefficients, and
when a ratio of each RGB component in the noted region is set as a, b, and c in no particular order (however, filling a≥b≥c), and each weighting coefficient corresponding to these is set a W_a, W_b, and W_c, W_a≤W_b≤W_c is true.

2. The image processing device according to claim 1, wherein
the input image is a video having a plurality of frames in a time sequence,
the weighting determination unit determines the weighting coefficients using the noted region in a current or past frame of the input image, and
the luminance calculation unit calculates luminance of each of the pixels in a current frame.

3. The image processing device according to claim 1, further comprising:
a first conversion unit and a second conversion unit, where
the first conversion unit converts an input image expressed in an RGB color space to an image expressed in a separate color space including brightness or luminance as a parameter, and
the second conversion unit inversely converts the image expressed in the separate color space to an output image expressed in the RGB color space, based on corrected brightness or corrected luminance as the luminance calculated by the luminance calculation unit, and based on a parameter other than brightness or luminance in the image converted by the first conversion unit.

4. The image processing device according to claim 1, further comprising:
a first conversion unit, a blend operation unit, and a second conversion unit, wherein:
the first conversion unit converts an input image expressed in an RGB color space to an image expressed in a separate color space including brightness or luminance as a parameter,
the blend operation unit calculates a correction brightness or correction luminance, which is a corrected brightness or corrected luminance, by blending brightness or luminance in the image converted by the first conversion unit and the luminance calculated by the luminance calculation unit at a prescribed blend ratio, and
the second conversion unit inversely converts to an output image expressed in an RGB color space based on the correction brightness or correction luminance and a parameter other than brightness or luminance in the image converted by the first conversion unit.

5. The image processing device according to claim 4, wherein the blend ratio is determined based on the ratio of the brightness or the luminance in the noted region in the image converted by the first conversion unit and the luminance calculated by the luminance calculation unit.

6. The image processing device according to claim 1, wherein the weighting determination unit respectively determines the weighting coefficients based on each difference between an overall average value of RGB components in the noted region and an average value of each RGB component.

7. The image processing device according to claim 6, wherein the weighting determination unit respectively determines the weighting coefficients based on a photograph of each difference, and
a function relating to the photograph includes an nth order function (n≥1), a logarithmic function, and an exponential function.

8. An image processing method, comprising:
a weighting determination step and a luminance calculation step, wherein
when a region made up of a plurality of pixels, which is at least one portion of an input image handled in the image processing method, is defined as a noted region, and this input image, either originally or as a result of an operation after being input, is an image expressed in an RGB color space, that is, each pixel is made up of an R component configuring red, a G component configuring green, and a B component configuring blue, and these are defined together as an RGB component,
in the weighting determination step, a weighting coefficient corresponding to each RGB component is respectively determined based on a quantity of each RGB component in the noted region,
in the luminance calculation step, luminance of each pixel included in the noted region is calculated based on each of the weighting coefficients, and
when a ratio of each RUB component in the noted region is set as a, b, and c in no particular order (however, fulfilling a≥b≥c), and each weighting coefficient corresponding to these is set as W_a, W_b, and W_c, W_a≤W_b≤W_c.

9. An image processing program for realizing a prescribed function in a computer, wherein
the prescribed function comprises a weighting determination function and a luminance calculation function,
when a region made up of a plurality of pixels, which is at least one portion of an input image input to the computer, is defined as a noted region, and this input image, either originally or as a result of an operation after being input, is an image expressed in an RGB color space, that is, each pixel is made up of an R component configuring red, a G component configuring green, and a B component configuring blue, and these are defined together as an RGB component,
according to the weighting determination function, a weighting coefficient corresponding to each RGB component is respectively determined based on a quantity of each RGB component in the noted region, according to the luminance calculation function, luminance of each pixel included in the noted region is calculated based on each of the weighting coefficients, and when a ratio of each RGB component in the noted region is set as a, b, and c in no particular order (however, fulfilling $a \geq b \geq c$), and each weighting coefficient corresponding to these is set as $W\_a$, $W\_b$, and $W\_c$, $W\_a \leq b \leq W\_c$ is true.

\* \* \* \* \*